(12) United States Patent
Whitchurch et al.

(10) Patent No.: US 7,745,677 B2
(45) Date of Patent: Jun. 29, 2010

(54) AROMATIC ISOMERIZATION CATALYST AND ISOMERIZATION PROCESS

(75) Inventors: Patrick C. Whitchurch, Bossier City, LA (US); Paula L. Bogdan, Mount Prospect, IL (US); John E. Bauer, LaGrange Park, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 12/608,367

(22) Filed: Oct. 29, 2009

(65) Prior Publication Data

US 2010/0137667 A1    Jun. 3, 2010

Related U.S. Application Data

(60) Division of application No. 11/965,925, filed on Dec. 28, 2007, now Pat. No. 7,629,283, which is a continuation-in-part of application No. 11/868,844, filed on Oct. 8, 2007.

(51) Int. Cl.
   *C07C 5/22* (2006.01)
(52) U.S. Cl. .................. 585/477; 585/480; 585/481; 585/482
(58) Field of Classification Search ................. 585/477, 585/480, 481, 482
See application file for complete search history.

(56) References Cited

U.S. PATENT DOCUMENTS

| | | | | |
|---|---|---|---|---|
| 4,962,259 A | * | 10/1990 | Sachtler et al. | ............. 585/480 |
| 2005/0277796 A1 | * | 12/2005 | Bogdan et al. | ............. 585/481 |
| 2008/0035525 A1 | * | 2/2008 | Burgfels et al. | ............... 208/26 |

* cited by examiner

*Primary Examiner*—Elizabeth D Wood
(74) *Attorney, Agent, or Firm*—David J Piasecki

(57) ABSTRACT

One exemplary embodiment can be an extruded C8 alkylaromatic isomerization catalyst. The extruded catalyst can include:
   about 2-about 20%, by weight, of an MTW zeolite;
   about 80-about 98%, by weight, of a binder including an alumina;
   about 0.01-about 2.00%, by weight, of a noble group metal calculated on an elemental basis; and
   about 100 ppm-less than about 1000 ppm, by weight, of at least one alkali metal calculated on an elemental basis.

Generally, the weight percents of the MTW zeolite, the binder, the noble group metal, and the at least one alkali metal are based on a weight of the extruded catalyst.

5 Claims, No Drawings

AROMATIC ISOMERIZATION CATALYST AND ISOMERIZATION PROCESS

CROSS-REFERENCE TO RELATED APPLICATIONS

This application is a Division of pending U.S. application Ser. No. 11/965,925, filed Dec. 28, 2007, which is a Continuation-In-Part of pending U.S. application Ser. No. 11/868,844, filed Oct. 8, 2007. U.S. application Ser. Nos. 11/965,925 and 11/868,844 are hereby incorporated by reference in their entirety.

FIELD OF THE INVENTION

The field of this invention generally relates to a catalyst for a C8 aromatic isomerization process or zone, and/or an isomerization process.

BACKGROUND OF THE INVENTION

The xylenes, such as para-xylene, meta-xylene and ortho-xylene, can be important intermediates that find wide and varied application in chemical syntheses. Generally, para-xylene upon oxidation yields terephthalic acid that is used in the manufacture of synthetic textile fibers and resins. Meta-xylene can be used in the manufacture of plasticizers, azo dyes, wood preservers, etc. Generally, ortho-xylene is feedstock for phthalic anhydride production.

Xylene isomers from catalytic reforming or other sources generally do not match demand proportions as chemical intermediates, and further comprise ethylbenzene, which can be difficult to separate or to convert. Typically, para-xylene is a major chemical intermediate with significant demand, but amounts to only 20-25% of a typical C8 aromatic stream. Adjustment of an isomer ratio to demand can be effected by combining xylene-isomer recovery, such as adsorption for para-xylene recovery, with isomerization to yield an additional quantity of the desired isomer. Typically, isomerization converts a non-equilibrium mixture of the xylene isomers that is lean in the desired xylene isomer to a mixture approaching equilibrium concentrations.

Various catalysts and processes have been developed to effect xylene isomerization. In selecting an appropriate technology, it is desirable to run the isomerization process as close to equilibrium as practical in order to maximize the para-xylene yield; however, associated with this is a greater cyclic C8 loss due to side reactions. Often, the approach to equilibrium that is used is an optimized compromise between high C8 cyclic loss at high conversion (i.e., very close approach to equilibrium) and high utility costs due to the large recycle rate of unconverted C8 aromatic. Thus, catalysts can be evaluated on the basis of a favorable balance of activity, selectivity and stability.

Catalysts can be made by several different processes. Generally, producing an extruded catalyst that can isomerize ethylbenzene to xylenes while minimizing C8 ring loss would be beneficial.

BRIEF SUMMARY OF THE INVENTION

One exemplary embodiment can be an extruded C8 alkylaromatic isomerization catalyst. The extruded catalyst can include:
about 2-about 20%, by weight, of an MTW zeolite;
about 80-about 98%, by weight, of a binder including an alumina;
about 0.01-about 2.00%, by weight, of a noble group metal calculated on an elemental basis; and
about 100 ppm-less than about 1000 ppm, by weight, of at least one alkali metal calculated on an elemental basis.

Generally, the weight percents of the MTW zeolite, the binder, the noble group metal, and the at least one alkali metal are based on a weight of the extruded catalyst.

Another exemplary embodiment can be an extruded C8 alkylaromatic isomerization catalyst. The extruded catalyst can include:
about 2-about 20%, by weight, of an MTW zeolite where the MTW zeolite may include about 4,000-about 8,000 ppm, by weight, of at least one alkali metal calculated on an elemental basis based on the weight of the zeolite;
about 80-about 98%, by weight, of a binder including an alumina; and
about 0.01-about 2.00%, by weight, of a noble group metal calculated on an elemental basis.

Generally, the weight percents of the MTW zeolite, the binder, and the noble group metal are based on a weight of the extruded catalyst.

A further exemplary embodiment is a process for isomerizing a non-equilibrium C8 aromatic feed to provide an isomerized product. The process can include contacting the non-equilibrium C8 aromatic feed with an extruded C8 alkylaromatic isomerization catalyst, and providing the isomerized product having a C8 ring loss of no more than about 2.5. Typically, the extruded catalyst includes:
about 2-about 20%, by weight, of an MTW zeolite;
about 80-about 98%, by weight, of a binder including an alumina;
about 0.01-about 2.00%, by weight, of a noble group metal calculated on an elemental basis; and
about 100 ppm-less than about 1000 ppm, by weight, of at least one alkali metal calculated on an elemental basis.

Generally, the weight percents of the MTW zeolite, the binder, the noble group metal, and at least one alkali metal are based on a weight of the extruded catalyst.

Therefore, the catalyst can provide lower C8 ring losses. In some exemplary embodiments, a catalyst with a higher alkali metal content by, e.g., omitting a catalyst wash, can yield a catalyst with a low C8 ring loss.

DEFINITIONS

As used herein, the term "zone" can refer to an area including one or more equipment items and/or one or more sub-zones. Equipment items can include one or more reactors or reactor vessels, heaters, separators, exchangers, pipes, pumps, compressors, and controllers. Additionally, an equipment item, such as a reactor or vessel, can further include one or more zones or sub-zones.

As used herein, the term "stream" can be a stream including various hydrocarbon molecules, such as straight-chain, branched, or cyclic alkanes, alkenes, alkadienes, and alkynes, and optionally other substances, such as gases, e.g., hydrogen, or impurities, such as heavy metals. The stream can also include aromatic and non-aromatic hydrocarbons. Moreover, the hydrocarbon molecules may be abbreviated C1, C2, C3 ... Cn where "n" represents the number of carbon atoms in the hydrocarbon molecule.

As used herein, the term "aromatic" can mean a group containing one or more rings of unsaturated cyclic carbon radicals where one or more of the carbon radicals can be replaced by one or more non-carbon radicals. An exemplary aromatic compound is benzene having a C6 ring containing three double bonds. Other exemplary aromatic compounds can include para-xylene, ortho-xylene, meta-xylene and ethylbenzene. Moreover, characterizing a stream or zone as "aromatic" can imply one or more different aromatic compounds.

As used herein, the term "support" generally means a molecular sieve that has been combined with a binder before the addition of one or more additional catalytically active components, such as a noble metal, or a subsequent process such as reducing or sulfiding.

DETAILED DESCRIPTION OF THE INVENTION

Generally, a refinery or a petrochemical production facility can include an aromatic production facility or an aromatic complex, particularly a C8 aromatic complex that purifies a reformate to extract one or more xylene isomers, such as para-xylene or meta-xylene. Such an aromatic complex for extracting para-xylene is disclosed in U.S. Pat. No. 6,740,788 B1. A feedstock to an aromatic complex can include an isomerizable aromatic hydrocarbon of the general formula $C_6H_{(6-n)}R_n$, where n is an integer from 2 to 5 and R is $CH_3$, $C_2H_5$, $C_3H_7$, or $C_4H_9$, in any combination and including all the isomers thereof. Suitable aromatic hydrocarbons may include ortho-xylene, meta-xylene, para-xylene, ethylbenzene, ethyltoluene, tri-methylbenzene, di-ethylbenzene, tri-ethylbenzene, methylpropylbenzene, ethylpropylbenzene, di-isopropylbenzene, or a mixture thereof.

An aromatic complex can include a xylene isomer separation zone, such as a para-xylene separation zone, and a C8 aromatic isomerization zone. The C8 aromatic isomerization zone can receive a stream depleted of at least one xylene isomer, such as para-xylene or meta-xylene. The C8 aromatic isomerization zone can reestablish the equilibrium concentration of xylene isomers and convert other compounds, such as ethylbenzene, into a xylene. Typically, such a zone can increase the amount of a xylene isomer, such as para-xylene, and the product from that C8 aromatic isomerization zone can be recycled to the xylene isomer separation zone to recover more of the desired isomer.

One exemplary application of the catalyst disclosed herein is the isomerization of a C8 aromatic mixture containing ethylbenzene and xylenes. Generally, the mixture has an ethylbenzene content of about 1-about 50%, by weight, an ortho-xylene content of up to about 35%, by weight, a meta-xylene content of about 20-about 95%, by weight, and a para-xylene content of up to about 30%, by weight. The aforementioned C8 aromatics are a non-equilibrium mixture, i.e., at least one C8 aromatic isomer is present in a concentration that differs substantially from the equilibrium concentration at isomerization conditions. Usually the non-equilibrium mixture is prepared by removal of para-, ortho- and/or meta-xylene from a fresh C8 aromatic mixture obtained from an aromatic production process.

Accordingly, a C8 aromatic hydrocarbon feed mixture, preferably in admixture with hydrogen, can be contacted with a catalyst hereinafter described in an C8 aromatic hydrocarbon isomerization zone. Contacting may be effected using the catalyst in a fixed bed system, a moving bed system, a fluidized bed system, or in a batch operation. Preferably, a fixed bed system is utilized. In this system, a hydrogen-rich gas and the feed mixture are preheated by any suitable heating means to the desired reaction temperature and then passed into a C8 aromatic isomerization zone containing a fixed bed of catalyst. The conversion zone may be one or more separate reactors with suitable means therebetween to ensure that the desired isomerization temperature is maintained at the entrance of each zone. The reactants may be contacted with the catalyst bed in either upward-, downward-, or radial-flow fashion, and the reactants may be in the liquid phase, a mixed liquid-vapor phase, or a vapor phase when contacted with the catalyst.

The feed mixture, preferably a non-equilibrium mixture of C8 aromatics, may be contacted with the isomerization catalyst at suitable C8 isomerization conditions. Generally, such conditions include a temperature ranging from about 0-about 600° C. or more, preferably about 300-about 500° C. Generally, the pressure is from about 100-about 10,000 kPa absolute, preferably less than about 5,000 kPa. Sufficient catalyst may be contained in the isomerization zone to provide a liquid hourly space velocity with respect to the hydrocarbon feed mixture of from about 0.1-about 30 hr$^{-1}$, and preferably about 0.5-about 10 hr$^{-1}$. The hydrocarbon feed mixture can be reacted in admixture with hydrogen at a hydrogen/hydrocarbon mole ratio of about 0.5:1-about 25:1 or more. Other inert diluents such as nitrogen, argon and light hydrocarbons may be present.

The reaction can isomerize xylenes while reacting ethylbenzene to form a xylene mixture via conversion to and reconversion from naphthenes. Thus, the yield of xylenes in the product may be enhanced by forming xylenes from ethylbenzene. Typically, the loss of C8 aromatics through the reaction is low, generally less than about 4%, by mole, preferably no more than about 3.5%, by mole, and most preferably less than about 3%, by mole, per pass of C8 aromatics in the feed to the reactor.

Any effective recovery scheme may be used to recover an isomerized product from the effluent of the reactors. Typically, the liquid product is fractionated to remove light and/or heavy byproducts to obtain the isomerized product. Heavy byproducts can include aromatic C10 compounds such as dimethylethylbenzene. In some instances, certain product species such as ortho-xylene or dimethylethylbenzene may be recovered from the isomerized product by selective fractionation. The product from isomerization of C8 aromatics usually is processed to selectively recover the para-xylene isomer, optionally by crystallization. Selective adsorption can be accomplished by using crystalline aluminosilicates according to U.S. Pat. No. 3,201,491.

A catalyst of the C8 aromatic isomerization zone can include at least one MTW zeolitic molecular sieve, also characterized as "low silica ZSM-12" and can include molecular sieves with a silica to alumina ratio less than about 45, preferably from about 20-about 40. Preferably, the MTW zeolite is substantially mordenite-free, which generally means an MTW component containing less than about 20%, by weight, mordenite impurity, preferably less than about 10%, by weight, and most preferably less than about 5%, by weight, mordenite.

The preparation of an MTW zeolite by crystallizing a mixture including an alumina source, a silica source and a templating agent is known. U.S. Pat. No. 3,832,449 discloses an MTW zeolite using tetraalkylammonium cations. U.S. Pat. No. 4,452,769 and U.S. Pat. No. 4,537,758 disclose a methyltriethylammonium cation to prepare a highly siliceous MTW zeolite. U.S. Pat. No. 6,652,832 uses an N,N-dimethylhexamethyleneimine cation as a template to produce low silica-to-alumina ratio MTW zeolite without MFI impurities. Preferably high purity crystals are used as seeds for subsequent batches.

The MTW zeolite is preferably composited with a binder for convenient formation of particles. The proportion of zeolite in the catalyst is about 1-about 90%, by weight, preferably about 2-about 20%, by weight, and optimally about 5-about 10%, by weight. Generally, it is desirable for the MTW zeolite to contain about 0.3-about 0.5%, by weight, $Na_2O$ and about 0.3-about 0.5%, by weight, $K_2O$. On an elemental basis, the MTW zeolite can contain about 4,000-8,000 ppm, by weight, of at least one alkali metal, preferably sodium and/or potassium. Typically, the MTW zeolite can contain about 2,000-about 4,000 ppm, by weight, sodium and about 2,000-about 4,000 ppm, by weight, potassium calculated on an elemental basis. Also, in one exemplary embodiment it is desirable for the molar ratio of silica to alumina to be about 36:1 and the molar ratio of (Na+K)/Al to be about 0.2-about 0.3.

Generally, the zeolite is combined with a refractory inorganic oxide binder. The binder should be a porous, adsorptive support having a surface area of about 25-about 500 $m^2/g$, preferably about 200-about 500 $m^2/g$. Desirably, the inorganic oxide is an alumina, such as a gamma-alumina. Such a gamma-alumina can be derived from a boehmite or a pseudo-boehmite alumina (hereinafter collectively may be referred to as "boehmite alumina"). The boehmite alumina can be compounded with the zeolite and extruded. During oxidation (or calcination), the boehmite alumina may be converted into gamma-alumina. One desired boehmite alumina utilized as a starting material is VERSAL-251 sold by UOP, LLC of Des Plaines, Ill. Another boehmite alumina can be sold under the trade designation CATAPAL C by Sasol North America of Houston, Tex. Generally, the catalyst can have about 10-about 99%, by weight, desirably about 90-about 99%, by weight, of the gamma-alumina binder. Similarly, the catalyst can include about 80-about 98%, by weight, preferably about 90-about 95%, by weight, of an alumina binder.

The alumina binder can have up to about 100 ppm sodium, up to about 200 ppm calcium, and up to about 200 ppm magnesium, by weight, calculated on an elemental basis based on the weight of the binder. Generally, the VERSAL-251 alumina can have up to about 100 ppm sodium, up to about 200 ppm calcium, and up to about 200 ppm magnesium, by weight, calculated on an elemental basis based on the weight of the binder. Typically, the CATAPAL C alumina can have up to about 30 ppm sodium, up to about 50 ppm calcium, and up to about 20 ppm magnesium, by weight, calculated on an elemental basis based on the weight of the binder.

One shape for the support or catalyst can be an extrudate. Generally, the extrusion initially involves mixing of the molecular sieve with optionally the binder and a suitable peptizing agent to form a homogeneous dough or thick paste having the correct moisture content to allow for the formation of extrudates with acceptable integrity to withstand direct calcination. Extrudability may be determined from an analysis of the moisture content of the dough, with a moisture content in the range of from about 30-about 70%, by weight, being preferred. The dough may then be extruded through a die pierced with multiple holes and the spaghetti-shaped extrudate can be cut to form particles in accordance with known techniques. A multitude of different extrudate shapes is possible, including a cylinder, cloverleaf, dumbbell, and symmetrical and asymmetrical polylobates. Furthermore, the dough or extrudates may be shaped to any desired form, such as a sphere, by, e.g., marumerization that can entail one or more moving plates or compressing the dough or extrudate into molds.

Alternatively, support or catalyst pellets can be formed into spherical particles by accretion methods. Such a method can entail adding liquid to a powder mixture of zeolite and binder in a rotating pan or conical vessel having a rotating auger.

Generally, preparation of alumina-bound spheres involves dropping a mixture of molecular sieve, alsol, and gelling agent into an oil bath maintained at elevated temperatures. Examples of gelling agents that may be used in this process include hexamethylene tetraamine, urea, and mixtures thereof. The gelling agents can release ammonia at the elevated temperatures which sets or converts the hydrosol spheres into hydrogel spheres. The spheres may then be withdrawn from the oil bath and typically subjected to specific aging treatments in oil and an ammonia solution to further improve their physical characteristics. One exemplary oil dropping method is disclosed in U.S. Pat. No. 2,620,314.

Generally, the subsequent drying, calcining, and optional washing steps can be done before and/or after impregnation with one or more components, such as metal. Preferably after formation of the binder and zeolite into a support, the support can be dried at a temperature of about 50-about 320° C., preferably about 100-about 200° C. for a period of about 1-about 24 hours or more. Next, the support is usually calcined or oxidized at a temperature of 50-about 700° C., desirably about 540-about 650° C. for a period of about 1-about 20 hours, desirably about 1-about 1.5 hours in an air atmosphere until the metallic compounds, if present, are converted substantially to the oxide form, and substantially all the alumina binder is converted to gamma-alumina. If desired, the optional halogen component may be adjusted by including a halogen or halogen-containing compound in the air atmosphere. The various heat treating steps may be conducted multiple times such as before and after addition of components, such as one or more metals, to the support via impregnation as is well known in the art. Steam may be present in the heat treating atmospheres during these steps. During calcination and/or other heat treatments to the catalyst, the pore size distribution of the alumina binder can be shifted to larger diameter pores. Thus, calcining the catalyst can increase the average pore size of the catalyst.

Optionally, the catalyst can be washed. Typically, the catalyst can be washed with a solution of ammonium nitrate or ammonium hydroxide, preferably ammonium hydroxide. Generally, the wash is conducted at a temperature of about 50-about 150° C. for about 1-about 10 hours. In one desired embodiment, no wash is conducted to provide an elevated level of at least one alkali metal. Generally, a wash of ammonium nitrate can lower the amount of alkali metal in the catalyst, particularly the zeolite. Exemplary catalysts without a wash are depicted in US Pub. No. 2005/0143615 A1. Preferably, no wash or a wash of ammonium hydroxide is conducted to allow much of the existing alkali metal to remain on the catalyst. It should be understood, however, if the zeolite and/or binder, particularly the zeolite, has an elevated alkali metal content then an ammonium nitrate wash can be conducted that allows some alkali metal at a desired level to remain on the zeolite and/or binder.

In some exemplary embodiments, after drying, calcining, and optionally washing, one or more components can be impregnated on the support. The catalyst may also include a noble metal, including one or more of platinum, palladium, rhodium, ruthenium, osmium, and iridium. The preferred noble metal is platinum. The noble metal component may exist within the final catalyst as a compound such as an oxide, sulfide, halide, or oxysulfide, or as an elemental metal or in combination with one or more other ingredients of the catalyst. Desirably, the noble metal component exists in a reduced state. This component may be present in the final catalyst in any amount which is catalytically effective. Generally, the final catalyst includes about 0.01-about 2%, desirably about 0.05-about 1%, and optimally about 0.25-about 0.5%, by weight, calculated on an elemental basis of the noble metal, preferably platinum.

The noble metal component may be incorporated into the catalyst in any suitable manner. One method of preparing the catalyst involves the utilization of a water-soluble, decomposable compound of a noble metal to impregnate the calcined sieve-binder composite. Alternatively, a noble metal compound may be added at the time of compositing the sieve component and binder. Complexes of noble metals that may be employed in impregnating solutions, co-extruded with the sieve and binder, or added by other known methods can include chloroplatinic acid, chloropalladic acid, ammonium chloroplatinate, bromoplatinic acid, platinum trichloride, platinum tetrachloride hydrate, platinum dichlorocarbonyl dichloride, tetramine platinic chloride, dinitrodiaminoplatinum, sodium tetranitroplatinate (II), palladium chloride, palladium nitrate, palladium sulfate, diaminepalladium (II) hydroxide, and tetraminepalladium (II) chloride.

A Group IVA (IUPAC 14) metal component may also be incorporated into the catalyst. Of the Group IVA (IUPAC 14) metals, germanium and tin are preferred and tin is especially preferred. This component may be present as an elemental metal, as a chemical compound such as the oxide, sulfide, halide, or oxychloride, or as a physical or chemical combination with the porous carrier material and/or other components of the catalyst. Preferably, a substantial portion of the Group IVA (IUPAC 14) metal exists in the finished catalyst in an oxidation state above that of the elemental metal. The Group IVA (IUPAC 14) metal component optimally is utilized in an amount sufficient to result in a final catalyst containing about 0.01-about 5%, by weight, preferably about 0.1 to about 2%, by weight, and optimally about 0.3-about 0.45, by weight, metal calculated on an elemental basis.

The Group IVA (IUPAC 14) metal component may be incorporated in the catalyst in any suitable manner to achieve a homogeneous dispersion, such as by co-precipitation with the porous carrier material, ion-exchange with the carrier material or impregnation of the carrier material at any stage in the preparation. One method of incorporating the Group IVA (IUPAC 14) metal component into the catalyst involves the utilization of a soluble, decomposable compound of a Group IVA (IUPAC 14) metal to impregnate and disperse the metal throughout the porous carrier material. The Group IVA (IUPAC 14) metal component can be impregnated either prior to, simultaneously with, or after the other components are added to the carrier material. Thus, the Group IVA (IUPAC 14) metal component may be added to the carrier material by commingling the latter with an aqueous solution of a suitable metal salt or soluble compound such as stannous bromide, stannous chloride, stannic chloride, stannic chloride pentahydrate; germanium oxide, germanium tetraethoxide, or germanium tetrachloride; or lead nitrate, lead acetate, or lead chlorate. The utilization of Group IVA (IUPAC 14) metal chloride compounds, such as stannic chloride, germanium tetrachloride or lead chlorate, is particularly preferred since they can facilitate the incorporation of both the metal component and at least a minor amount of the preferred halogen component in a single step. When combined with hydrogen chloride during the especially preferred alumina peptization step as described above, a homogeneous dispersion of the Group IVA (IUPAC 14) metal component can be obtained. In an alternative embodiment, organic metal compounds such as trimethyltin chloride and dimethyltin dichloride are incorporated into the catalyst during the peptization of the alumina with hydrogen chloride or nitric acid.

The catalyst may also contain other metal components as well. Such metal modifiers may include rhenium, cobalt, nickel, indium, gallium, zinc, uranium, dysprosium, thallium, or a mixture thereof. Generally, a catalytically effective amount of such a metal modifier may be incorporated into a catalyst to effect a homogeneous or stratified distribution.

The catalyst can also contain a halogen component, such as fluorine, chlorine, bromine, iodine or a mixture thereof, with chlorine being preferred. Desirably, the catalyst contains no added halogen other than that associated with other catalyst components.

The catalyst may also contain at least one alkali metal with a total alkali metal content of the catalyst of at least about 100 ppm, by weight, calculated on an elemental basis. The alkali metal can be lithium, sodium, potassium, rubidium, cesium, francium, or a combination thereof. Preferred alkali metals can include sodium and potassium. Desirably, the catalyst contains no added alkali metal other than that associated with the zeolite and/or binder. Generally, the total alkali metal content of the catalyst is at least about 200 ppm, desirably 300 ppm, by weight, calculated on an elemental basis. Generally, the total alkali metal content of the catalyst is no more than about 2500 ppm, desirably 2000 ppm, and optimally 1000 ppm, by weight, calculated on an elemental basis. In one preferred embodiment, the catalyst can have about 300 ppm-about 2500 ppm, by weight, of at least one alkali metal calculated on an elemental basis. In a further embodiment, the catalyst can have about 100 ppm-less than about 1000 ppm, preferably about 300-less than about 1000 ppm, and optimally about 300-about 700 ppm, by weight, of at least one alkali metal, preferably sodium and/or potassium, calculated on an elemental basis. In yet another preferred embodiment, the catalyst can have at least about 150 ppm, preferably about 150-about 310 ppm, by weight, sodium and at least about 50 ppm, and preferably about 50-about 250 ppm, by weight, potassium, calculated on an elemental basis.

The resultant catalyst can subsequently be subjected to a substantially water-free reduction step to ensure a uniform and finely divided dispersion of the optional metallic components. The reduction may be effected in the process equipment of the aromatic complex. Substantially pure and dry hydrogen (i.e., less than about 100 vol. ppm, preferably about 20 vol. ppm, $H_2O$) preferably is used as the reducing agent. The reducing agent can contact the catalyst at conditions, including a temperature of about 200-about 650° C. and a period of about 0.5-about 10 hours, effective to reduce substantially all of the Group VIII metal component to the metallic state. In some cases, the resulting reduced catalyst may also be beneficially subjected to presulfiding by a known method such as with neat $H_2S$ at room temperature to incorporate in the catalyst an amount of about 0.05-about 1.0%, by weight, sulfur, calculated on an elemental basis.

The elemental analysis of the components of the zeolite and/or catalyst, such as noble metal component and/or the at least one alkali metal can be determined by Inductively Coupled Plasma (ICP) analysis according to UOP Method 961-98. The elemental analysis of an alkali metal, such as sodium, in an alumina binder, such as V-251 binder, can be conducted by ICP or atomic adsorption spectroscopy analysis. Regarding atomic adsorption spectroscopy analysis, sodium content can be determined according to UOP Method 410-85 and potassium content can be determined according to UOP Method 878-87.

Generally, catalysts described herein have several beneficial properties that provide isomerization of ethylbenzene while minimizing C8 ring-loss. Although not wanting to be bound by theory, it is generally thought that the higher levels (greater than about 100 ppm, by weight, calculated on an elemental basis based on the weight of the catalyst) of at least one alkali metal can reduce C8 ring loss. Thus, contacting a non-equilibrium C8 aromatic feed with an extruded C8 alkylaromatic isomerization catalyst can provide an isomerized product with a C8 ring loss of no more than about 2.5, about 2.0-about 2.5, or about 2.5.

In addition, a catalyst described herein generally has a piece density of less than about 1.250 g/cc, preferably of less than about 0.950 g/cc, more preferably of less than about 0.900 g/cc, and optimally about 0.800-about 0.890 g/cc as determined by mercury displacement according to UOP-766-91. Furthermore, the catalyst described herein generally has a surface area (may be referred herein as BET-SA) of at least about 190 m$^2$/g, preferably at least about 210 m$^2$/g, and optimally about 220-about 250 m$^2$/g as determined by UOP-874-88. All the UOP methods, such as UOP 410-85, UOP-766-91, UOP-874-88, UOP 878-87 and UOP-961-98, discussed herein can be obtained through ASTM International, 100 Barr Harbor Drive, West Conshohocken, Pa., USA.

Illustrative Embodiments

The following examples are intended to further illustrate the subject catalyst. These illustrations of embodiments of the invention are not meant to limit the claims of this invention to the particular details of these examples. These examples are based on engineering calculations and actual operating experience with similar processes.

The exemplary catalysts can have a commercially synthesized MTW zeolite and an alumina source of either VERSAL-251 sold by UOP, LLC, an alumina sold under the trade designation CATAPAL C by Sasol North America of Houston, Tex., or an aluminum hydroxychloride hydrosol (alsol or ODS alumina). All of these alumina sources can be converted to gamma alumina by heat treatment, yet they have different properties and performance. Although the VERSAL-251 (V-251) and CATAPAL C, which are both boehmite aluminas normally used to prepare extrudates, and the alsol is normally used to prepare oil dropped spheres, generally the ultimate catalyst shape is not determined by the alumina source. Spherical catalysts can be prepared from boehmite alumina binders and oil dropped spheres may be formed into extrudates.

To form the extrudate supports, the alumina is usually at least partially peptized with a peptizing agent such as nitric acid. The zeolite can be mixed with the at least partially peptized alumina or may be mixed with the alumina prior to peptization. Afterwards, typically the alumina and MTW zeolite mixture is extruded into a cylinder or a tri-lobe shape. That being done, the extrudate can be dried and then calcined at about 540-about 650° C. for about 60-about 90 minutes.

The catalysts can be washed with ammonium nitrate or ammonium hydroxide, or not washed. If washed, the catalyst may be washed at a temperature of 90° C. for 5 hours. For an ammonium nitrate solution, the solution can include 1 g of ammonium nitrate and 5.7 g of water per gram of catalyst. For an ammonium hydroxide solution, 0.5%, by weight, of NH$_3$, in water can be used. The washing step may be conducted on the formed and calcined support prior to addition of the noble metal.

To form the oil-dropped support, an MTW zeolite is mixed with alsol. Generally, the alsol and MTW zeolite mixture is mixed with a gelling agent of hexamethylene tetraamine. Afterwards, the spheres can be formed and aged in the oil-dropping process. Next, the ODS supports may be washed with about 0.5% ammonia, and calcined at about 540-about 650° C. for about 90 minutes.

The following can be undertaken for both the extruded supports and the ODS supports. Namely, all the supports can be impregnated with platinum with a solution of chloroplatinic acid mixed with water and HCl. Generally, the HCl is in an amount of 2%, by weight, of the support, and the excess solution is evaporated.

Next, the supports can be oxidized or calcined at a temperature of about 565° C. for about 60-about 120 minutes in an atmosphere of about 5-about 15 mol % of steam with a water to chloride ratio of about 50:1-about 120:1.

Generally afterwards, the supports are reduced at about 565° C. for about 120 minutes in a mixture of at least about 15 mol % hydrogen in nitrogen. That being done, the supports can be sulfided in a 10 mol % atmosphere of hydrogen sulfide in a hydrogen sulfide and hydrogen mixture at ambient conditions to obtain about 0.07%, by weight, sulfur on the support to obtain the final catalysts. A depiction of the materials and methods for forming the exemplary catalysts is provided in the table below:

TABLE 1

| Catalyst Example No. | Support Type | Shape | Forming Method | Alumina Source | Amount MTW Weight % | Wash |
|---|---|---|---|---|---|---|
| A1 | IX'd CB | Trilobe | Extrusion | V-251 | 5 | NH$_4$OH |
| A2 | CB | Trilobe | Extrusion | V-251 | 5 | None |
| A3 | IX'd CB | Trilobe | Extrusion | V-251 | 5 | NH$_4$NO$_3$ |
| A4 | IX'd CB | Cylindrical | Extrusion | V-251 | 5 | NH$_4$NO$_3$ |
| A5 | CB | Trilobe | Extrusion | V-251 | 10 | None |
| A6 | CB | Trilobe | Extrusion | V-251 | 10 | None |
| A7 | IX'd CB | Trilobe | Extrusion | V-251 | 10 | NH$_4$NO$_3$ |
| A8 | IX'd CB | Trilobe | Extrusion | V-251 | 10 | NH$_4$OH |
| A9 | CB | Trilobe | Extrusion | V-251 | 5 | None |
| B1 | CB | Sphere | Oil Dropping | ODS | 5 | NH$_4$OH |
| B2 | CB | Sphere | Oil Dropping | ODS | 5 | NH$_4$OH |
| B3 | IX'd CB | Cylinder | Extrusion | ODS | 5 | NH$_4$NO$_3$ |
| C1 | IX'd CB | Cylinder | Extrusion | Catapal C | 5 | NH$_4$NO$_3$ |
| C2 | IX'd CB | Cylinder | Extrusion | Catapal C | 5 | NH$_4$OH |

As used in the table, the term "CB" refers to a calcined base including the binder and zeolite, and the term "IX'd CB" refers to a calcined base washed with a solution of NH$_4$OH or NH$_4$NO$_3$, as depicted in the "Wash" column for that row in TABLE 1.

The following data are depicted for the reduced catalysts in the following table. The LOI is conducted in accordance with UOP-275-98. All components are provided in percent, by weight.

TABLE 2

| Catalyst Example No. | LOI @ 900° C. Weight % | Cl Weight % | Pt Weight % | Si Weight % | Na Weight % | K Weight % |
|---|---|---|---|---|---|---|
| A1 | 1.45 | 0.61 | 0.326 | 2.24 | 0.021 | 0.015 |
| A2 | 0.86 | 0.74 | 0.458 | 2.25 | 0.022 | 0.015 |
| A3 | 0.34 | 0.58 | 0.314 | 2.28 | 0.003 | <0.005 |
| A4 | 0.95 | 0.61 | 0.309 | 2.26 | 0.003 | <0.005 |
| A5 | 0.10 | 0.62 | 0.313 | 3.55 | 0.030 | 0.025 |
| A6 | 0.70 | 0.65 | 0.450 | 3.55 | 0.031 | 0.025 |
| A7 | 0.53 | 0.58 | 0.316 | 3.58 | 0.004 | <0.005 |
| A8 | 0.47 | 0.59 | 0.315 | 3.62 | 0.025 | 0.021 |
| A9 | 0.60 | 0.04 | 0.310 | 2.27 | 0.036 | 0.031 |
| B1 | 1.14 | 0.49 | 0.311 | 2.45 | 0.008 | <0.005 |
| B2 | 1.45 | 0.63 | 0.300 | 2.28 | 0.009 | <0.005 |
| B3 | 1.40 | 0.57 | 0.324 | 2.10 | <0.002 | <0.005 |
| C1 | 1.00 | 0.67 | 0.320 | 2.24 | <0.002 | <0.005 |
| C2 | 0.58 | 0.61 | 0.308 | 2.24 | 0.014 | 0.012 |

Moreover, the reduced catalysts are evaluated for several property measurements, as depicted below:

TABLE 3

| Catalyst Example No. | Piece Density (Volatile Free) g/cc | BET-SA square-meter/gram | % Pore Volume Greater Than 100 Å % |
|---|---|---|---|
| A1 | 0.868 | 230 | 81 |
| A2 | 0.869 | 247 | 72 |
| A3 | 0.869 | 223 | 83 |
| A4 | 0.839 | 226 | 83 |
| A5 | 0.874 | 242 | 81 |
| A6 | 0.872 | 239 | 81 |
| A7 | 0.886 | 237 | 81 |
| A8 | 0.879 | 242 | 80 |
| A9 | 0.867 | 223 | 83 |
| B1 | 0.924 | 208 | 86 |
| B2 | 0.969 | 208 | — |
| B3 | 0.909 | 193 | 88 |
| C1 | 1.209 | 216 | 61 |
| C2 | 1.203 | 207 | 65 |

The amount of sodium and potassium in the MTW zeolite and the amount of sodium in the binder in the reduced catalysts before sulfiding are depicted below:

TABLE 4

| Catalyst Example No. | MTW Na Weight % | MTW K Weight % | Alumina Source | Alumina Na Weight % |
|---|---|---|---|---|
| A1 | 0.224 | 0.265 | V-251 | 0.0079 |
| A2 | 0.224 | 0.265 | V-251 | 0.0079 |
| A3 | 0.224 | 0.265 | V-251 | 0.0079 |
| A4 | 0.224 | 0.265 | V-251 | 0.0079 |
| A5 | 0.224 | 0.265 | V-251 | 0.0079 |
| A6 | 0.224 | 0.265 | V-251 | 0.0079 |
| A7 | 0.224 | 0.265 | V-251 | 0.0079 |
| A8 | 0.224 | 0.265 | V-251 | 0.0079 |
| A9 | 0.564 | 0.555 | V-251 | 0.0079 |
| B1 | 0.224 | 0.265 | ODS | — |
| B2 | 0.224 | 0.265 | ODS | — |
| B3 | 0.224 | 0.265 | ODS | — |
| C1 | 0.224 | 0.265 | Catapal C | N/A |
| C2 | 0.224 | 0.265 | Catapal C | N/A |

Most of the catalysts from Table 2 are sulfided and evaluated for C8 aromatic ring loss using a pilot plant flow reactor processing a non-equilibrium C8 aromatic feed having the following approximate composition in percent, by weight:

TABLE 5

| Feed Composition | |
|---|---|
| Component | Weight % |
| Ethylbenzene | 14 |
| Para-xylene | <1 |
| Meta-xylene | 55 |
| Ortho-xylene | 22 |
| Toluene | 1 |
| C8 Paraffins | <1 |
| C8 Naphthenes | 6 |
| Water | 100-200 ppm |

This feed is contacted with a catalyst at a pressure of about 700 kPa(g), a weight hourly space velocity (may be referred to as WHSV) of 8.0 hr$^{-1}$, and a hydrogen/hydrocarbon mole ratio of 4. The reactor temperature is about 385° C.

The "C8 ring loss" is in mole percent as defined as "(1−(C8 naphthenes and aromatics in product)/(C8 naphthenes and aromatics in feed))*100", which represents a loss of one or more C8 rings that can be converted into a desired C8 aromatic, such as paraxylene. This loss of feed generally requires more feed to be provided to generate a given amount of product, reducing the profitability of the unit. Generally, a low amount of C8 ring loss is a favorable feature for a catalyst. The "C8 ring loss" (may be abbreviated herein as "C8RL") can be measured in the table below at conversion of the following formula:

$$pX/X*100\% = 22.2 \pm 0.05\%$$

where:

pX represents moles of para-xylene in the product; and

X represents moles of xylene in the product.

Generally, the WHSV is set at 8 hr$^{-1}$ at the start of the test and is increased until pX/X*100%=22.2±0.05%. Exemplary catalysts are tested in the pilot plant for C8 ring loss with the following results:

TABLE 6

| Catalyst Example No. | Na + K PPM | C8RL Mole % | WHSV |
|---|---|---|---|
| A1 | 360 | 2.1 | 9.7 |
| A2 | 370 | 2.1 | 11.0 |
| A3 | <80 | 2.4 | 11.5 |
| A4 | <80 | 2.6 | 9.7 |
| A5 | 550 | 2.3 | 17.0 |
| A6 | 560 | 2.3 | 17.0 |
| A7 | <90 | 3.0 | 18.0 |
| A8 | 460 | 2.4 | 15.0 |
| A9 | 670 | 2.0 | 6.4 |

TABLE 6-continued

| Catalyst Example No. | Na + K PPM | C8RL Mole % | WHSV |
|---|---|---|---|
| B1 | <130 | 2.6 | 10.7 |
| B3 | <70 | 3.0 | 12.0 |
| C1 | <70 | 3.4 | 10.2 |
| C2 | 260 | 2.6 | 9.7 |

As depicted above, the C8 ring loss is compared with the total alkali metal content at a given WHSV. Catalysts having more than about 200 ppm of sodium and potassium and derived from VERSAL-251 alumina have C8RL values ranging from 2.0-2.4 mole percent with an average C8RL of 2.2 mole percent. These values are substantially lower than the C8RL values for either catalysts derived from CATAPAL C alumina (ranging from 2.6-3.4 mole percent and averaging 3.0 mole percent) or an ODS alumina (ranging from 2.6-3.0 mole percent and averaging 2.8 mole percent).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing, all temperatures are set forth uncorrected in degrees Celsius and, all parts and percentages are by weight, unless otherwise indicated.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for isomerizing a non-equilibrium C8 aromatic feed to provide an isomerized product, comprising:
  A) contacting the non-equilibrium C8 aromatic feed with an extruded C8 alkylaromatic isomerization catalyst, wherein the extruded catalyst comprises:
    1) about 2-about 20%, by weight, of an MTW zeolite;
    2) about 80-about 98%, by weight, of a binder comprising an alumina;
    3) about 0.01-about 2.00%, by weight, of a noble group metal calculated on an elemental basis; and
    4) about 100 ppm-less than about 1000 ppm, by weight, of at least one alkali metal calculated on an elemental basis;
  wherein the weight percents of the MTW zeolite, the binder, the noble group metal, and at least one alkali metal are based on a weight of the extruded catalyst; and
  B) providing the isomerized product having a C8 ring loss of no more than about 2.5.

2. The process according to claim 1, wherein the isomerized product has a C8 ring loss of about 2.0-about 2.5.

3. The process according to claim 1, wherein the at least one alkali metal comprises sodium and the extruded catalyst comprises at least about 150 ppm, by weight, of sodium calculated on an elemental basis based on the weight of the extruded catalyst.

4. The process according to claim 1, wherein the at least one alkali metal comprises potassium and the extruded catalyst comprises at least about 50 ppm, by weight, of potassium calculated on an elemental basis based on the weight of the extruded catalyst.

5. The process according to claim 1, wherein the extruded catalyst comprises:
  about 5-about 10%, by weight, of the MTW zeolite; and
  about 90-about 95%, by weight, of the binder;
  wherein the weight percents of the MTW zeolite and the binder are based on the weight of the extruded catalyst.

* * * * *